United States Patent [19]
Speaker et al.

[11] Patent Number: 5,686,113
[45] Date of Patent: Nov. 11, 1997

[54] MICROCAPSULES OF PREDETERMINED PEPTIDE(S) SPECIFICITY (IES), THEIR PREPARATION AND USES

[75] Inventors: Tully J. Speaker; Kenneth J. Sultzbaugh, both of Philadelphia, Pa.

[73] Assignee: Temple University of the Commonwealth System of Higher Education, Philadelphia, Pa.

[21] Appl. No.: 408,052

[22] Filed: Mar. 21, 1995

[51] Int. Cl.$^6$ .............................. A61K 9/16; A61K 9/50
[52] U.S. Cl. .................... 424/490; 424/491; 424/492; 424/493; 424/494; 424/497
[58] Field of Search .................... 424/490, 491, 424/492, 493, 494, 495, 497

[56] References Cited

U.S. PATENT DOCUMENTS

| | | | |
|---|---|---|---|
| 3,137,631 | 6/1964 | Soloway | 424/491 |
| 3,959,457 | 5/1976 | Speaker et al. | 424/1.25 |
| 4,205,060 | 5/1980 | Monsimer et al. | 424/495 |
| 4,606,940 | 8/1986 | Frank et al. | 427/213.32 |
| 4,744,933 | 5/1988 | Rha et al. | 264/4.3 |
| 5,132,117 | 7/1992 | Speaker et al. | 424/490 |

FOREIGN PATENT DOCUMENTS 2135954  9/1984  United Kingdom.

OTHER PUBLICATIONS

J.D. Andrade et al., "Coated adsorbents for direct blood perfusion: HAMA/activated carbon", *Trans. Amer. Soc. Artif. Int. Organs.* 17:222–228 (1971).

F. Lim & Sun, "Microencapsulated Islets as Bioartificial Endocrine Pancreas", *Science* 210:908–910 (1980).

Gref et al., "Biodegradable Long–Circulating Polymeric Nanospheres", *Science* 263:1600–1603 (1994).

Torchilin et al., "Targeted accumulation of polyethylene glycol–coated Immunoliposomes in Infected rabbit myocardium", *J. Fed. Amer. Soc. Expl. Biol.* 6:2716–2719 (1992).

Illum et al., *Biomaterials* 8:113 (1987).

Lee et al., "Protein Adsorption on Pluronic Copolymer Coated Polystyrene Particles", *J. Colloid Interface Sci.* 131:252–266 (1989).

Lehr, C.M. et al., "Bioadhesion by Means of Specific Binding of Tomato Lectin", *Pharm. Res.* 9:547–553 (1992).

Urdal and Hakomori "Tumor–associated Ganglio–N–triosylceramide", *J. Biol. Chem.* 255:10509–10515 (1980).

Weinstein et al., "Antibody Medicated Targeting of Liposomes Binding to Lymphocytes Does Not Insure Incorporation of Vesicle Contents into Cells", *B. B. A.* 509:272–288 (1978).

Leserman et al., "Binding of Antigen–Bearing Fluorescent Liposomes to the Murine Myeloma Tumor MOPC 315", *J. Immunol.* 122:585–591 (1979).

Rivnay and Wilchek, "Use of Avidin–Biotin Technology for Liposome Targeting", in *Methods in Enzymology* 149:119–123 (1987).

*Primary Examiner*—Nathan M. Nutter
*Attorney, Agent, or Firm*—Ratner & Prestia

[57] ABSTRACT

An aqueous core microcapsule has a capsular wall provided with a peptide(s) of pre-determined binding specificity(ies) appended to the surface, the wall being the reaction product of an anionic polymer or salt thereof and a polyamine, salt thereof, mixtures thereof, or mixtures thereof with monoamines. The aqueous core may contain an active ingredient(s), and be targeted for delivery to specific cell tissues. The microcapsules are provided as a composition and in a kit with instructions for use in imaging, diagnosis, therapy, vaccination, and other applications.

42 Claims, No Drawings

MICROCAPSULES OF PREDETERMINED PEPTIDE(S) SPECIFICITY (IES), THEIR PREPARATION AND USES

BACKGROUND OF THE INVENTION

1. Field of the Invention

This invention relates to the field of in vivo delivery of active agents. More particularly, this invention relates to microcapsules prepared by the reaction of Lewis acid and base wall-forming reactants, targeted for the delivery of encapsulated ingredient(s).

2. Description of the Background

Microcapsules are fine dispersions of solids or droplets of liquid onto which a thin film coating has been applied. The average diameter of microcapsules may vary from one micron to several hundred microns depending on the materials used and their method of production. The term nanocapsule is usually applied to similar constructs having average diameters of less than one micron. Microspheres can be differentiated over microcapsules in that they do not possess distinct core and coating regions, but have the ingredient(s) to be delivered and adjuvant, if present, uniformly distributed throughout the bulk of the particle. The term microparticle is often used to describe constructs which cannot be readily placed into either of the above two categories or as a generic term for both. If the constructs are less than one micron in diameter, then the corresponding terms nanosphere and nanoparticle are often utilized.

Microencapsulation is a process by which a relatively thin coating can be applied to dispersions of small particles of solids or droplets of liquids. This process provides a means for converting liquids to solids, and for altering colloidal and surface properties while avoiding environmental damage, and controlling the release characteristics or availability of coated materials. Several of these properties can be attained by macropackaging techniques. The uniqueness of microencapsulation, however, resides in the smallness of the resulting coated particles, and their subsequent adaptation to a wide variety of dosage forms and use in multiple product applications. Up to the present time, known methods for producing microcapsules on an industrial scale have often involved the use of organic solvents, even though the use of the latter may present environmental and safety problems, and their removal is often difficult and, if incomplete, leaves organic contaminants.

In U.S. Pat. No. 3,137,631 water-insoluble organic liquids are encapsulated by cross-linking synthetic resins with the aid of heat or catalysts, or both. The capsule shells are described as formed from covalently linked non-ionic materials or from heat denaturable proteins, while the cross-linking is said to stabilize the resulting capsules. U.S. Pat. No. 4,205,060 discloses microcapsules comprising a core containing a water-soluble salt formed from polymeric ionic resin and a medicament. The medicament salt is formed either by reaction of an acidic polymer with a basic medicament or, a basic polymer with an acidic drug. The walls of the microcapsules are formed from water-insoluble film-forming polymers. The film-forming polymers identified as suitable sheathing agents are all water-insoluble, neutral, non-ionized polymers. The capsules of the prior patent are made by preparing an aqueous solution of a salt made by reacting a medicament and a core polymer, placing a water-insoluble sheath-forming polymer in a first water-immiscible organic liquid, dispersing the aqueous solution in the organic solution, and adding to the dispersion a second water-immiscible liquid, which does not act as a solvent for the sheath-forming polymer, to precipitate the film around droplets of the dispersed aqueous phase.

In U.S. Pat. No. 4,606,940, microcapsules are prepared by coacervation and precipitation of the encapsulating material with the aid of temperature changes. A single colloid is dispersed in water and the water of solvation is removed from the colloid by addition of chemical compounds having greater affinity for water than the colloid, causing the colloid chains to come closer together and form a coacervate. U.S. Pat. No. 3,959,457 to Speaker et al. forms microcapsules by reacting in a low boiling point, polar, organic solvent, a finely dispersed emulsion, a water-immiscible solution of an organic polyfunctional Lewis base, and an aqueous solution of a partially hydrophilic, partially lipophilic, polyfunctional Lewis acid. These capsules have lipophilic cores and carry pharmaceuticals, such as quinacrine. A modification of the technology disclosed in U.S. Pat. No. 3,959,457, is described in U.S. Pat. No. 5,132,117, where a lipophilic surfactant, such as sorbitan trioleate is added to the organic phase prior to emulsification, causing an inversion of the two phases. Thus, the aqueous phase becomes encapsulated while the organic phase remains outside the microcapsules as a continuous phase.

Yet another method of producing microcapsules introduced droplets of an aqueous anionic polymer, such as sodium carboxymethylcellulose, and a material to be encapsulated, into an aqueous alkylamine salt, such as stearylamine hydrochloride. The reagents react at the droplet boundary to form a water-insoluble wall, the size of which may be varied by varying the size of the polymer solution droplets. The film forming the wall is formed at a "pseudo-interface" between the two aqueous solutions.

Belgium Patent No. 882,476 to Lim, describes the formation of calcium alginate microspheres, surface-treating them to form polylysine or polyethylenimine alginate coacervates, and then core-liquifying them with a calcium chelating agent. U.S. Pat. No. 4,744,933 to Rha & Rodrigues-Sanchez simplifies the Lim process by spraying one charged polymer directly into an oppositely charged polymer to produce a complex coacervate thereby obtaining a similar product. U.K. Patent Application 2,135,954A by Dautzenberg et al. discloses the formation of complex coacervate microcapsules by causing anionic polymer solution droplets to fall into solutions of oppositely charged poly-quaternary ammonium salts.

Many of the previously known entirely aqueous systems were based on the formation of coacervates, and provide microbeads of widely ranging particle size. Some require strongly acidic media, e.g., pH 3–4, to precipitate proteinaceous coacervates. More complex coacervates precipitate from aqueous solution of two oppositely charged polymers. Hydrogels based on aqueous hydroxyethylacrylate involve free radical polymerization, catalyzed by peroxy species or ionizing radiation, which may be destructive of fragile protein molecules or intact organisms, but suitable for delivery of other materials (Andrade, et al, Trans. Amer. Soc. Artif. Int. Organs 17:222–228 (1971)). Alginic acid and calcium ion hydrogels may be formed by a process that is suitable for enveloping both microbes and multicellular organisms such as nematodes (Lim & Sun, Science 210:908–910 (1980)).

Most microparticulate delivery systems available are not surface modified. In consequence, their particles, when used for imaging or delivering therapeutic agents, are rapidly engulfed by the reticuloendothelial system. For example, albumin or galactose microspheres have been employed for imaging purposes. These microspheres are cleared from blood in about 20 seconds. Polyoxyethylene esters linked to the surface of polylactide-coglycolide microspheres are modified microspheres which are less prone to be eliminated by the reticuloendothelial system when compared to the non-modified polylactide-coglycolide microspheres. Polyoxamer and polysorbate have been attached to polystyrene and polymethylmethacrylate microspheres to reduce phagocytosis by the reticuloendothelial system. Although polyoxyethylene coatings are useful in avoiding phagocytosis by the reticuloendothelial system, they lack specific binding characteristics. (Gref et al., Science 263: 1600–1603, (1994); Torchilin et al., J. Fed. Amer. Soc. Expl. Biol. 6: 2716 (1992); Illum. et al., Biomaterials 8: 113 (1987); Lee et al., J. Colloid Interface Sci. 131:252 (1989)). In addition, the above microcapsular forms have low core loading capacities and, consequently, low efficiency of capture of active material during manufacture.

Tomato lectin was adsorbed to polystyrene beads (Lehr, C. M., et al., Pharm. Res. 9: 547–553 (1992)). Although polystyrene beads adhere to enterocytes, they have been shown to be ineffective as carriers for drugs. Indirect targeting has been reported utilizing avidin to bridge biotin-substituted drugs (Urdal and Hakomori, J. Biol. Chem. 255: 10509–10515 (1980)). Liposomes have been derivatized with avidin-biotin bridged antibodies bound to cells (Urdal and Hakomori (1980); Weinstein et al, B. B. A. 509: 272–288 (1978); Leserman et al., J. Immunol. 122: 585–591 (1979); Rivnay and Wilchek, in Methods in Enzymology, Vol. 149, pp. 119–123, Academic Press Inc. (1987)). However, although targeting appears to have been attained in many cases, the release of the active ingredient proved difficult at best. In addition, liposomes have an extremely low loading capacity and their preparation includes non-aqueous steps. In general, drug-carrying targeted liposomes rely heavily for their activity on the tendency of lymphatic cells to phagocytize foreign particles of a certain size range. The targeting, however, fails to extend to cells other than phagocytic cells.

Accordingly, there is still a need for a microcapsule system, which is specifically targeted and has a high loading efficiency, whose preparation is mild enough to spare the core ingredient(s) from damage, and is effective in releasing their content at the desired site.

SUMMARY OF THE INVENTION

This invention relates to microcapsules comprising an aqueous core surrounded by a capsular wall having a surface provided with peptide(s) linked thereto, the peptide(s) having a free segment(s) of pre-determined binding specificity (ies) and the wall comprising the reaction product of a polymer having a plurality of anionic residues or a salt thereof and a monomer having a plurality of amine residues, a salt thereof, mixtures thereof, and mixtures thereof with a monoamine(s). The microcapsules may contain one or more active ingredients, and may be fluorescently labeled and/or color coded to facilitate their identification, detection or location of the encapsulated formulations.

This invention also relates to a kit for delivering the encapsulated active ingredient(s), comprising the microcapsules of the invention, and instructions for its use. The ingredient loaded into the capsules and microcapsules of a therapeutic kit is generally a therapeutic agent(s), a vaccine (s), cells for lost-function replacement, and the like. A diagnostic or imaging kit generally has as the core ingredient (s) dyes, fluorophores, electron opaque agents, energy emitting materials, and pigments, among others, and an agricultural kit has core ingredients such as pesticides.

This invention discloses a method of preparing the peptide-derivatized microcapsules of the invention, and a method of using the microcapsules of this invention for the targeted delivery of active ingredients, such as dyes, vaccines, agricultural agents, pharmaceutical agents, and the like.

DESCRIPTION OF THE PREFERRED EMBODIMENTS

The present invention arose from a desire to improve on prior technology which, in addition to encapsulating products, would provide a way of delivering them to specific sites on soluble molecules, cells and/or tissues of immunologic and other origins. The present invention utilizes microencapsulation technology, supplemented by derivatization of the microcapsules with a peptide(s) of defined specificity(ies). The capsules and microcapsules of the invention have aqueous cores surrounded by capsular walls provided with peptide(s) linked to the surface of the walls having a free segment(s) of predetermined binding specificity(ies), the wall comprising the reaction product of an anionic Lewis acid polymer or salt thereof with a polycationic Lewis base, salt thereof, or a mixture with a monocationic Lewis base. The thus derivatized microcapsules may be produced as particles of substantially uniform size under gentle conditions, and may be loaded with active ingredients such as therapeutic drugs, agricultural products, vaccines, diagnostic agents, and the like. The microcapsules may have attached to their capsular wall a peptide(s) such as aidin, avidin, streptavidin, antibodies, antigens, protein G, protein A, and the like, an intermediary in the preparation of the final product, where the peptide(s) may be antibodies, antigens, lectins, and the like.

The present microcapsules may be utilized, for example, in methods and kits suitable for in vivo imaging, diagnosis, prophylaxis, and therapy of certain diseases, as well as for implementing replacement therapy to a predetermined tissue, while avoiding widespread dissemination of the encapsulated agent. In addition, the present microcapsules find utility in the agricultural and immunization fields. The present invention is, for example, useful in the targeted delivery, slow release, and maintenance of uniform therapeutic concentration of proteins and peptides such as enzymes, e.g., glucose 6-phosphate dehydrogenase, proteins such as calcitonin, erythropoietin, insulin, interleukin and somatotropin, among others, macromolecules such as heparin, vaccines and vaccine components derived from intact or immunogenic subunits, including "naked" deoxyribonucleic acid (DNA) and deoxyribonucleic acid constructs, and/or derived from intact or attenuated organisms or their immunogenic subunits, including actinomyces, bacilli, cocci, fungi, helminths, larvae, prions, protozoa, rickettsia, spirochetes, viruses, and yeasts, tolerizing antigens used for immunization against, or attenuation of, allergic responses, to dusts, danders, pollens, spores, and the like, and cells such as pancreatic islet cells, hepatocytes, interleukin- and other immunomoudulator-secreting cells derived from human or other species, and partially and fully synthetic derivatives and analogues thereof, when administered or implanted to serve as surrogates for damaged, dysfunctional or missing tissues and/or organs which, if not encapsulated, might be recognized as foreign to the recipient organism and subject to unwanted immunologic attack. This invention also permits the targeted delivery, slow release, and maintenance of uniform therapeutic concentrations of numerous drugs, particularly highly irritant drugs, e.g., fluorouracil, at a rate slow enough to reduce their toxicity, anti-inflammatory agents such as prednisolone, flurbiprofen, and indomethacin, antibiotics such as tetracycline, and antispasmodic drugs such as theophylline, among others. When used to encapsulate pigmented or opaque materials, such as blue dextran or charcoal, the present capsules and microcapsules may be applied to the protection of light-sensitive bioactive agents, such as invermectin (an ectoparasiticide) and Bt proteins (B. thuringiensis larvacidal proteins), among others, and to their subsequent release, either gradually or in triggered bursts.

The delivery of many drugs, such as anti-neoplastic agents via microcapsules targeted to a diseased tissue may enhance their therapeutic efficacy by increasing the concentration of drug in the targeted tissue over all other regions. Thus, by properly titrating the administered dose, an effective drug concentration may be achieved in the target tissue while sparing other tissues from unnecessary and potentially harmful, even toxic, concentrations of the drug. For example, the cardiotoxicity of the anti-neoplastic agent doxorubicin, which is potentially life-threatening, is diminished by delivering the drug in microcapsules targeted to the tumor rather than by achieving high concentrations of the drug throughout the body. Antibiotic-laden microcapsules, for example, are useful to fight infection and infestation. The present microcapsules may, for example, carry microorganism- or parasite-specific lectins or antibodies attached to the capsular wall. The microcapsules of the invention may, furthermore, have fluorophores attached to the microcapsular wall to aid in the visualization of specific cell types, to which the targeted microcapsules attach. The microcapsules of this invention may also carry, attached to the capsular wall, antibodies which selectively bind to microorganisms, such as HIV, and the like. These microcapsules are, thus, directed to attach to HIV-infected T-cells or their synctial forms. Active ingredient(s) suitable for this type of application are anti-sense oligonucleotides, inhibitors of transcriptases, and inhibitors of essential cellular enzymatic processes, among others.

The microcapsule of the invention comprises an aqueous core surrounded by a capsular wall provided with a peptide (s) linked thereto, which has a free segment(s) of pre-determined binding specificity(ies), the wall comprising the reaction product of a polymer having a plurality of anionic residues or salt thereof and a monomer having a plurality of amine residues, salts thereof, mixtures thereof, and mixtures thereof with monoamine. The microcapsules of the invention are well suited for carrying active ingredient(s), and due to their modified surface, for delivering them to a target. The attachment of the proteinaceous moieties or peptides to the capsular wall may be attained by linking a peptide residue with excess anionic or amine capsular residues. The peptide (s) may be attached to the capsular wall either directly or by means of linking agents, and may be a targeting peptide comprising a free segment of pre-determined specificity, or be an intermediate linking agent, which is a member of a binding pair. And the other member of the binding pair, in turn, either comprises or is linked to a targeting peptide. Whether the free peptide segment(s) are attached directly, or through a binding pair, to the wall, they have a pre-determined specificity(ies) capable of selective attachment to certain macromolecules, cells, and/or tissues displaying on their surfaces characteristic epitopic markers. The microcapsules, thus, may adhere to target macromolecules, cells or tissues with a high degree of selectivity, useful for in vivo applications, such as immunization against, and diagnosis and treatment of, certain diseases in animals and plants. The pre-determined specificity of the microcapsules carrying a peptide member of a binding pair may also be applied to the selective separation of the other member, namely, the molecules, cells or tissues to which the peptide binds selectively. One pair of complementary materials, or binding pair, meeting these criteria are carbohydrates and lectins or carbohydrate-binding proteins. Other pairs of complementary materials meeting these criteria are antibodies, particularly monoclonal antibodies, and their antigens, polypeptides, such as protein A and G, and the Fc regions of antibodies, particularly immunoglobulin G, among others. Antibody-antigen binding pairs may be utilized in at least two manners. The antibody, or a fragment thereof containing its antigen binding site, may be attached to the capsular wall. In this case, the target for the microcapsules is the antigen present in the circulation or on a tissue or cell surface. Alternatively, the antigen, fragment or analogue thereof, may be appended to the capsular wall. This microcapsule will target antibodies or fragments thereof, which are bound to cells or in circulation.

The invention is generally and specifically described herein in reference to the carbohydrate-lectin pair, mostly for expediency and thoroughness. However, the teachings are applicable to any pair of complementary materials or binding pair presently in the public domain and to any other complementary materials which may become known hereafter. Carbohydrates, also known as saccharides or sugars, are a group of naturally occurring polyhydroxylated aldehydes and ketones. Characteristic carbodydrate monomers, oligomers, and polymers are attached to the outside surface of most, if not all, mammalian cells. One end of a saccharide is generally conjugated to membrane lipids or proteins while the other, often a branched end(s) typically extends into the extracellular fluid. Multiple sites of attachment on a single monosaccharide enable a large number of polysaccharides to be synthesized from only a few different types of monosaccharides. For example, four different monosaccharides may be linked together differently to form up to 35,560 unique tetrasaccharides. The carbohydrates expressed on each cell's surface are often characteristic of the cell type. Red blood cells, for example, of the four major blood types may be differentiated from one another by their characteristic polysaccharides.

Lectins, phytohemagglutinins, phytoagglutinins or agglutinins, are carbohydrate binding proteins or glycoproteins of non-immune origin which selectively agglutinate cells and precipitate glycoconjugates. Lectins accomplish these two effects by simultaneously binding to the carbohydrate epitopes of two or more cells or to the carbohydrate segments of two or more glycoconjugates. Lectins, therefore, must possess two or more carbohydrate binding sites per molecule (Goldstein et al., Nature 285:66 (1980)). Lectins may be isolated from a great variety of natural sources, both botanical and animal, including seeds, plant roots and bark, fungi, bacteria, viruses, seaweed, and sponges, molluscs, fish eggs, body fluids of invertebrates and lower vertebrates, and mammalian cell membranes. Two different systems of nomenclature are used to name lectins. In one system, the lectin is named after the source from which it is obtained, e.g., tomato lectin. In the other, the lectin is named after the monosaccharide which inhibits its binding to a known substrate, e.g. arabinose-binding lectin. Several commercially available lectins are listed herein by their taxonomic and common names, along with the carbohydrates to which they bind: Abrus precatorius (Jequirity bean), D-galNac; Ricinus communis (Castor bean), D-man, D-glc,GLcNAc; Canavalia ensiformis (Concanavalin A), GalNAc; Limulus polyphemus (Horshoe crab), α-L-fuc; Helix pomatia (Snail, edible), (D-glcNAc)$_3$; Vicia faba (Fava bean), D-galNAC; Vicia cracca (Common vetch), D-gal; Anguilla anguilla (Eel), D-galNAc, B-D-gal; Solanum tubersum (Potato), α-D-man, α-D-glc; Wisteria floribunda (Wisteria(Japan)), NeuNAc, D-galNAc, D-glcNAc; where gal: galactose, gc: glucose, man: mannose, galNAc: N-acetyl galactosamine, fuc: fucose, NeuNAc: N-acetyl neuraminic acid, glcNAc: N-acetyl glucosamine, man: mannose.

Other sugar-binding proteins such as sugar specific enzymes, e.g., glycosidases, glycosyltransferases, glycosylkinases, glycosylpermeases, and glycosylepimerases, transport proteins, hormones such as thyroid-stimulating hormone, and follicle-stimulating hormone, and toxins such as ricin, abrin, modeccin, and the like, may also be considered lectins if they have multiple combining sites, agglutinate cells and/or precipitate glycoconjugates. However, toxins which bear only one sugar-binding site are not considered lectins because they are unable to agglutinate cells or precipitate glycoconjugates. The selection of a lectin, having the appropriate specificity for a selected cell antigen to be targeted, may be attained by searching the literature. (For example, Bradley and Schnar, J. Leukocyte Biol. 40: 97–111 (1986); Sharon and Lis, Science 246:227–246 (1989); Ofek and Sharon, Current Topics in Microbiol. and Immunol. 151: 91–112, Springer-Verlag, Berlin, Heidelberg (1990); Yoshioka et al., J. Pharm. Sci. 82 (3): 273–275 (1993); Sharon & Lis, Science 177: 949–959 (1972)).

The lectin-carbohydrate interaction involves primarily hydrogen bonds and van der Waals forces. The association constants for the lectin-carbohydrate complexes are typically about 102 to 107 M. The selectivity of a lectin for a carbohydrate is provided by means of a precise stereochemical fit of the carbohydrate within a binding "pocket" of the lectin. While the carbohydrate molecule is in the lectin's carbohydrate-binding pocket, the carbohydrate hydroxyls are in close proximity to amino acid residues of the protein with which they may interact. Complementary pairs of carbohydrates and lectins function endogenously as recognition markers in many cell—cell interactions. Many types of epithelial tissues, e.g., lung, gastrointestinal, and genitourinary tissues, may be differentiated from one another by the polysaccharides displayed on their cell surfaces. Many pathogenic microorganisms, such as *E. coli* and *H. pylori*, express lectins on their outer surfaces, which enables them to adhere selectively to host tissues. This adhesion increases the likelihood of infection because it allows the microorganisms to resist the host's normal defense mechanisms. The selective binding of microorganisms to host tissues may also account for the greater likelihood of many pathogens to cause infection in some organs than in others. Given that carbohydrates and peptides function as cell markers, and the fact that lectins and antibodies, respectively, bind selectively to carbohydrates, and peptides, lectins and antibodies, are preferred embodiments of the peptide(s) attached to the capsular cell wall of the microcapsules of this invention. The peptide(s) may be attached to the excess amine or anionic residues of the capsular wall by means of a small linking molecule bridge, or through a binding pair, such as the biotin-avidin linking agent. Other suitable linking agents are antibody-antigens, Fc region of immunoglobulins-protein A or Fc region of immunoglobulins-protein G, among others.

The method employed herein to attach peptides, such as lectins, to the capsular walls involves the preparation of a predetermined type of microcapsules containing excess anionic or cationic residues, the conjugation of avidin to the surface of the microcapsules, and the incubation of the avidin-coated microcapsules with the biotin-lectin conjugate. One general method of binding peptide(s), e.g., lectins, to the capsular wall surface is provided herein, which takes advantage of the affinity of the glycoprotein avidin for the vitamin biotin (Green, N. M., in Advances in Protein Chemistry, London & N.Y., Academic Press, pp. 85–131 (1975a)). However, others may also be utilized within the confines of this invention. The attachment of a peptide(s), such as antibodies, lectins, antigens, avidin, streptavidin, and the like, to active amine residues on the capsular wall may be attained as described in the examples provided below or by other procedures known in the art (For example, Green N. M., Adv. Protein Chem., pp. 85–133 (1975); Yamada et al., Biochemistry 20: 4836–4842 (1981); Staros et al., Analytical Biochem. 156:220–222 (1986); Green N. M., Biochem. J. 94: 23C (1965)). The attachment of the peptide(s) to active anionic residues on the capsular wall, such as carboxylate, sulfate, sulfonate, phosphate, phosphamido, and the like, may be conducted by methods known in the art. Briefly, to attach antibodies to capsular surfaces provided with an excess of anionic functions, e.g. carboxylic acid groups, the same general approach as employed to bind antibodies to amine-rich surfaces may be used. Most simply, the carboxylate groups may be activated by reaction with a carbodiimide reagent, preferably a water soluble reagent such as 1-ethyl-3-(dimethylamino propyl)-carbodiimide hydrochloride, to generate an 0-acyl urea derivative. Subsequently, and in practice in situ, the 0-acyl urea derivative is allowed to react with N-hydroxysulfosuccinimide to generate the carboxylate ester of the hyroxysulfosuccinimide and split off the former carbodiimide as a urea derivative. An amino group from the antibody, e.g. an epsilon amino group from lysine, is then able to exert a nucleophilic attack on the highly activated carboxylate ester of the hydroxysuccinimide to form a new amide bond joining the capsule carboxylate to the antibody amine and regenerating N-hydroxysulfosuccinimide. In some instances the desired antibody may not have a suitably available free amino group to participate in the direct formation of a new amide bond joining capsule and antibody. In such instances, it is possible to couple the antibody to the capsular surface by using a low molecular diamine, such as 1,4-butylene diamine, to generate two new amide bonds, the first joining a capsular carboxylic acid to one amino group of the diamine and the second joining the other amino group of the diamine to a carboxylic acid group of the antibody. To prevent the reaction of both amino groups of a single diamine molecule with the carboxylate group groups of the capsular surface, it is desirable to utilize the diamine with one of its amino functions temporarily protected, e.g., in the form of a carbobenzoxy derivative. Thus, the protected amine may be covalently linked to the capsular surface through an amide bond using carbodiimide and N-hydroxysuccinimide reagents as described above. Following the formation of the first amide bond, the distal amino group of the diamine may be exposed by removing the carbobenzoxy moiety under mild reducing conditions and subsequently joined in a amide bond to a carboxylic acid group of the antibody by again using carbodiimide and N-hydroxysuccinimide reagents.

The lectins and other peptides are affixed to the capsular wall surface without altering their carbohydrate-binding capacity(ies). In accordance with this invention, the lectins and other peptides may be attached directly to the excess residues present on the surface of the microcapsules, e. g., through one of many cross-linking agents known in the art, such as bis (sulfosuccinimidyl) suberate, ethylene glycol-bis-(sulfosuccinimidyl succinate), bis [2-

(sulfosuccinimidoxy carbonyloxy) ethyl]sulfone, sulfosuccinimidy]-4-(p-maleidophenyl) butyrate, N-hydroxy sulfosuccinamide, ethyldimethyl amino propylcarbodiimide, or glutaraldehyde, among others, as is known in the art (Staros, J. B., Biochemistry 21: 3950–3955 (1982); Abdella, R. M., et al., Biochem. Biophys. Comm. 87: 734–42 (1979); Zarling, D. A., J. Immunol. 124: 913–920 (1980); Bangs, J. D., et al., J. Cell. Biol. 103: 255–263 (1986)). The utilization of cross-linking agents, such as the ones listed above, results in the formation of primary bonds linking the lectins or other peptides to the microcapsules. However, the direct binding of specific lectins and other peptides to the capsular wall surface may require that the cross-linking agent(s) and/or peptide(s) used, be modified because of the diverse amino acid sequences, molecular weight, and tertiary structure of the different peptides. The technology for attaching peptides to different wall residues, e.g., anionic or amine groups via a linker, is known in the art, and need not be fully detailed herein.

Avidin is a 67 Kdalton glycoprotein found in egg white, bird, reptile, and amphibian tissues. It is soluble in water and in salt solutions, and consists of four identical polypeptide subunits of 128 amino acids each. Each avidin subunit binds one molecule of biotin, with an interaction involving tryptophan and lysine. The protein is glycosylated at the Asn-17 residue, and contains about 10% w/w carbohydrate, mannose and N-acetyl galactosamine accounting for most of the carbohydrate. In addition, avidin contains one cysteine bond per subunit. The reduction of this sulfur bond does not alter the affinity of avidin for biotin. Streptavidin is a 60 Kdalton protein isolated form streptomyces avidinii, which is less water soluble than avidin. Streptavidin, like avidin, consists of four identical subunits, with each subunit binding one molecule of biotin. Biotin, also known as vitamin H, is a 244 Dalton water-soluble vitamin found in minute quantities in all living cells.

A carboxyl acid group is allowed to react with a carbodiimide to form an acyl urea which subsequently is allowed to react with a N-hydroxysuccinimide reagent to yield a hydroxyimide ester. The hydroxyimide is readily attacked by a free amino group to generate a new amide bond, regenerating the hydroxysuccinimide reagent. The biotin binding activity of avidin remains unaffected even by extensive chemical modification. The small size of biotin allows its conjugation to many proteins, such as lectins, antigens and antibodies, without loss of either function. The avidin-biotin interaction is, thus, used for a wide variety of purposes in which two different molecules must be joined together, with one of the two molecules being conjugated to avidin, and the other to biotin. The two conjugates are then incubated together in an aqueous medium, and joined together by an avidin-biotin "link."

A variety of water-soluble linking agents, such as 1-ethyl-3-(3-dimethyl aminopropyl)-carbodiimide hydrochloride (EDC), are suitable for the attachment of a peptide(s) to the capsular wall and are commercially available, especially when used in conjunction with N-hydroxy sulfosuccinimide and the linking agents described above. Similarly, a variety of water-soluble biotinylating agents, such as N-hydroxy sulfosuccinimide biotin (Sulfo-NHS-biotin), sulfosuccinimidyl-6-biotinamido hexanoate, and N-iodoacetyl-N'-biotinyl hexylene diamine, or other small molecules, such as p-hydroxy-benzeneazo-benzoic acid, among others, are also available to attach biotin to a member of the binding pair (Savage, et al, Avidin-Biotin Chemistry: A Handbook, Rockford, Pierce Chem. Co., pp. 132–133 (1992)). Antibodies and other protein molecules, such as protein A, Protein G, and antigens, among others, may be attached to the microcapsule in essentially the same manner as that employed to link avidin to the surface of the microcapsules.

Briefly, hydroxy sulfosuccinimide-derived reagents react with primary amino groups, e.g., lysine epsilon groups, through a nuclophilic attack on the hydroxysuccinimide to produce an amide bond. In the presence of a suitable carbodiimide reagent, free carboxylic acid groups react to form reactive imidoesters, which may subsequently react with free amino groups to give amide bonds and release the carbodiimide as a urea derivative. Iodoacetyl-based reagents react by nuclophilic substitutions of the iodine-carbon bond with a thiol group to produce stable thiol ester links.

The particular examples provided below include spermine alginate microcapsules, whose surfaces were modified by covalent attachment of avidin. The avidin-carrying microcapsules are subsequently linked through an avidin-biotin bond to biotinylated lectins derived from various sources, for example succinylated C. ensiformis, E. corallodendron, L. esculentum, V. villosa, P. vulgaris, G. max, and U. europeaus, among others. (Bragg, P. D. and Hou, C., Arch. Biochem. Biophys. 167: 311–322 (1975); Staros, I. V., Biochemistry 21:3950–55 (1982); Yamada, H., Biochemistry 20:4836–42 (1981); Suton, K., et al., J. Mol. Biol. 178: 323–39 (1984)). The thus modified microcapsules are able to bind specifically to carbohydrates, such as, beta-D-galactose-(1–3)-N-acetylgalactosamine, alpha-D-mannose, and alpha-D-glucose, alpha-D-mannose, and D-acetyl glucosamine dimer, and N-acetyl neuraminic acid, respectively.

In another embodiment, the microcapsules of the invention may include within the capsular wall surface, miniscule particles, e.g., 1 µm diameter, of a label, such as magnetic iron oxide, which permits the specific magnetic separation of targeted materials. Other labeled compounds, such as radionucleides, e.g., and $^3$H—, $^{14}$C—, $^{18}$F—, $^{32}$P—, $^{99m}$Tc—, and $^{125}$I—, may also be utilized for visualizing cells and tissues, to which the microcapsules have bound, by means of X-rays or magnetic resonance imaging.

Examples of anionic polymers are alginic acid, arabic acid, cellulose sulfate, carboxymethylcellulose, carrageenans, chondroitin sulfate, heparin, polyacrylic acid, polyoxyethylene cross-linked polyacrylic acid, polyphosphazine, glycolic acid esters of polyphosphazine, lactic acid esters of polyphosphazine, hyaluronic acid, polygalacturonic acid, polyphenylene sulfonic acid, and polyvinylcarboxylic acid, among others, derivatives thereof and mixtures thereof. Others, however, are also suitable.

Amines suitable for use in the preparation of the capsular wall are di-, tri-, tetra-, and higher amines, mixtures thereof, and mixtures thereof with monoamines. When the excess residues comprise amine residues, the amines utilized are preferably tri-, tetra- or higher amines or their mixtures with other amines, including monoamines. Examples of monomers with a plurality of amine residues are ($C_1$–$C_{16}$) alkylene diamines, ($C_1$–$C_{16}$) alkylene triamines, ($C_1$–$C_{16}$) alkylene tetraamines, ($C_1$–$C_{16}$) alkylene pentaamines, and the like, and examples of monoamines are ($C_1$–$C_{16}$) alkylene monoamines. Others, however, are also suitable. Examples of monomers with multiple amine residues are ethylenediamine, propylenediamine, butylenediamine, pentylenediamine, hexanediamine, piperazine, triethylenetetramine, diethylenetriamine, spermidine, methylene blue, and spermine, and examples of monoamines are decylamine, dodecylamine, tetradecylamine, hexadecylamine, octadecylamine, and didecylamine. Preferred amines with a plurality of residues are spermine, spermidine, diethylenetriamine, ethylenediamine, butylenediamine, dodecyldiamine, and triethylenetetraamine, and preferred monoamines are decylamine, dodecylamine, tetradecylamine, hexadecylamine, octadecylamine, and didecylamine. Di and oligo-functional amines react readily with anionic polymers to form the capsular wall. In addition, they also react readily with linking agents, such as carbodiimide, which may be utilized to attach peptides to the capsular wall. A preferred group of monomers with a plurality of amine residues are those where at least one of the amino residues comprises a primary amino group. The proportion of the amine monomers may vary broadly, but in preferred embodiment, the amine monomers comprise triamines and monoamines in a molar ratio of about 0.6 to 0.9 and about 0.4 to 0.1, respectively, and in another preferred embodiment, the amine monomers comprise tetraamines and monoamines in a molar ratio of about 0.6 to 0.9, and about 0.4 to 0.1, respectively. Preferably, the total amount of amine remains the same, and, generally, when the amount of monoamines is increased, the amount of polyamines is decreased. However, other combinations are also suitable.

Useful combinations of anionic polymers and di- tri- tetra- amine reagents which form microcapsules in accordance with the present invention are displayed in Table 1 below together with monoamines, which in some instances may be usefully included, preferably in a mole ratio up to about 0.4 of the total amine content.

another preferred type of microcapsule is that where the wall comprises alginic acid and spermine. Still another preferred microcapsule is that where the anionic polymer comprises chondroitin sulfate and the amine comprises spermine.

Typically, the anionic polymer has an average molecular weight greater than about 50 Kdaltons, and preferably greater than about 12 Kdaltons. In one case the anionic polymer may have linked thereto a fluorophore, such as fluorescein, rhodamine, and Texas red, among others. The anionic polymers are preferably employed as their neutral salts with an alkali metal ion, e.g., sodium, and the amines are preferably in the form of their chloride or acetate salts. However, both anionic and amine compounds may be utilized as such.

The lectin-carrying microcapsules are suitable for use in the treatment of cancerous tissues, whose cell surfaces have identifiable peptide antigens containing specific carbohydrates (Muramatsee, T., Glycobiology 3: 294–6 (1993); Itzkowitz, S. H. et al., Cancer 66: 1960–6 (1990); Leathem, A. J. and Brooks, S. A., Lancet 1054–6 (1987); Hiraizumi, S. et al., J. Cancer Res. 83: 1063–72 (1992)). Similarly, microcapsules provided with antibodies, preferably monoclonal antibodies, having a specificity which allows them to bind to, e.g., tumor cells, with greatly enhanced strength when compared to normal tissues, are also preferred. A large number of antibodies are commercially available and may be identified as to type and vendor through commercial directories (e.g., Linscott's Directory, 4877 Grange Road, Santa Rosa, Calif. 95404). Alternatively, antibodies may be prepared by immunizing a mammalian host with an antigen,

TABLE 1

Amine/Polymer Combinations Forming Stable Microcapsules

| Amines | (E.W.) | p-acrylic acid | p-vinylcarboxylic acid | alginic acid | Eudragit L-100 | cellulose sulfate | carboxymethylcellulose | heparin | chondroitin sulfate | cellulose acetate phthalate | arabic |
|---|---|---|---|---|---|---|---|---|---|---|---|
| Anionic Polymers (E.W.) | | (74) | (86) | (176) | (185) | (260) | (295) | (480) | (480) | (563) | (1000) |
| ethylenediamine | (30) | + | + | 0 | 0 | + | 0 | 0 | 0 | 0 | 0 |
| triethylenetetramine | (37) | + | + | + | 0 | + | 0 | 0 | 0 | 0 | 0 |
| piperizine | (43) | 0 | 0 | + | 0 | 0 | 0 | 0 | 0 | 0 | 0 |
| spermine | (51) | + | + | + | + | + | + | + | + | 0 | 0 |
| arginine | (87) | 0 | + | 0 | 0 | 0 | 0 | 0 | 0 | 0 | 0 |
| triethylamine | (95) | + | 0 | 0 | 0 | 0 | 0 | 0 | 0 | 0 | 0 |
| decylamine | (156) | + | + | + | + | + | + | + | + | 0 | + |
| dodecylamine | (170) | + | + | + | + | + | + | + | + | 0 | + |
| tetradecylamine | (184) | + | + | + | + | + | + | + | + | 0 | + |
| methylene blue | (187) | 0 | + | + | 0 | + | 0 | 0 | 0 | 0 | 0 |
| hexadecylamine | (198) | + | + | + | + | + | + | + | + | 0 | + |
| octadecylamine | (212) | + | + | + | + | + | + | + | + | 0 | + |

A plus mark (+) indicates the reactants will form microcapsules, a zero indicates they do not.

A preferred group of microcapsules are those where the anionic polymer comprises polyacrylic acid, polyvinylcarboxylic acid, alginic acid, carborymethyl cellulose, chondroitin sulfate, heparin, hyaluronic acid, polygalacturonic acid and cellulose acid sulfate, or mixtures thereof, and the amine comprises ethylene/amine, spermidine, spermine, triethylenetetramine, mixtures thereof, or mixtures thereof with monoamines. One particularly preferred the of microcapsule is that where the wall is formed of alginic acid and spermine. Another preferred type of microcapsule is that comprised of polyacrylic acid and diaminobutane. Still analogues or fragments thereof, and collecting the host's B-lymphocytes producing the antibodies as is known in the art. The B-lymphocytes may then be fused with immortal cells, such as myeloma cells, and the like, to produce hybridomas expressing monoclonal antibodies of a predetermined single specificity (Kohler and Milstein, Nature 256: 495–497 (1975)). Other methods of producing monoclonal antibodies are also known in the art. Antigens for binding to the capsular wall, may be obtained from specialized tissues or cells, e.g., from the cell membrane or by synthesizing specific sequences known to be expressed by a specialized cell. The thus prepared microcapsules are targeted to antibodies or fragments thereof, which are expressed by specialized cells, and are present in the host's circulation, or are found protruding from the cell surface.

The microcapsules of the invention may be loaded with an active ingredient in their aqueous core. Any active ingredient that generally administered to the organism to which the microcapsules are delivered may be utilized. Core materials suitable for use in this invention are polypeptides, non-peptide polymers, cells and fragments thereof, pharmaceutical agents, dyes, human and animal vaccines, labeling agents, agricultural agents, animal health agents, magnetic materials, image-enhancing materials, radioactive materials, pesticides, pheromones, photoprotective agents, which may be employed as adjuvants or principal active ingredients, and pigments, among others. Polypeptides suitable as core ingredients in the microcapsules of the invention are all polypeptides and proteins which are not lethal to the host. In some instances, however, the polypeptide may, in fact, be harmful to the targeted cell types, e.g., in the case of anti-microbial drugs. Other polypeptides suitable for use as the active ingredient are glucose 6-phosphate dehydrogenase, calcitonin, erythropoietin, insulin, interleukin, somatotropin, asparaginase, lactase, cellulase, trypsine, lipase, collagenase, streptodornase, streptokinase, tissue plasminogen activator, and larvacidal proteins of *B. thuringiensis*. Similarly, any non-peptide macromolecule that is not lethal to the host may be utilized in the microcapsules of the invention. Examples are heparin, synthetic and semi-synthetic analogues thereof, hirudin and fragments thereof, and anti-sense polynucleotides, among others. Any type of cell, except those that may be lethal to the host, may be carried by the microcapsules of the invention. Examples are pancreatic islet cells, hepatocytes, thyroid cells, parathyroid cells, gonadal cells, adrenocortical cells, and interlukin- and other immunogulator-secreting cells, among others. The delivery of the macromolecules, whether polypeptides or non-peptide macromolecules, in an encapsulated form, minimizes the exposure of antigenic sites of the macromolecules to the host's immunological system. In this manner, any inter-species immunological reaction is either greatly diminished or eliminated. Even if an inter-species immunological reaction appears, it is reduced and will not interfere, for instance, with single-treatment diagnostic, and vaccination applications, among others. Other pharmaceutical agents may also be utilized, and examples are anti-neoplastic agents, radionuclides, anti-inflammatories, antibiotics, anti-fungal agents, anti-helmintic agents, anti-protozoal agents, hypoglycemic agents, among others. Dyes, pigments, and other labeling agents are also suitable for targeted delivery. Examples are dextran blue, phenol red, iron oxide, charcoal, chlorophyll, eosin, erythrosin, fluorescein, rhodamine, Texas red, and trypan blue, among others. Other examples are charcoal, fluorouracil, indomethacin, nicotinamide, phenol red, prednisolone, tetracycline, theophylline, larvacidal proteins of Bacillus thuringiensis (Bt) subsp. israelensis, and strains of viruses represented by the envelope and non-envelope viruses vaccinia and rotavirus, respectively, among others. In addition, human and veterinary vaccines and strains of rotaviruses, examples of which are listed in Tables 2 to 4 below, may also be utilized as core materials in accordance with the present invention.

TABLE 2

| Human vaccines | |
|---|---|
| Diptheria toxoid | Respiratory syncytial virus |
| Petrussis toxoid | Adenovirus |
| Tetanus toxoid | Parainfluenza virus |
| Hepatitis B surface antigen | *Streptococcus pneumoniae* |
| Hepatitus A virus | Canaraypox recombinants |
| Influenza virus (live or inactivated) | Yellow fever virus |
| Live attenuated pollovirus | Rables virus |
| Inactivated poliovirus | Cholera |
| Hemophilus Influenza type B | *Yersinia pestis* (plague) |
| *Neisseria meningitidis* | *Salmonella typhi* (typhoid) |
| Measles | BCG |
| Mumps | |
| Rubella | |
| Varicella | |

TABLE 3

| Rotavirus Strains |
|---|
| Bovine WC3 |
| HCR3a |
| Bovine WC3, modified with Human VP4 W179 |
| Bovine WC3, modified with Human W178-8 |
| Bovine WC3, modified with Human W179-9 and SC2 |
| Bovine WC3, modified with Human W179 |
| Bovine WC3, modified with Human VP4 SC2 |
| Bovine WC3, modified with Human vp4 Bricot B |

TABLE 4

| Veterinary vaccines | |
|---|---|
| Cattle Viruses | Cattle Bacteria |
| Infectious *bovine rhinotracheitis* | Haemophilus/Pasturella species |
| Parainfluenza type 3 | Leptospira |
| Bovine diarrhea virus | Ciostridia species |
| Bovine respiratory synctial virus | Tetanus toxoid |
| Rotavirus | |
| Coronavirus | |
| Rabies | |
| Dog Viruses | Dog Bacteria |
| Canine distemper/measles | *Borrelia burgdorferi* |
| *Canine hepatitis* | Leptospira |
| Parvovirus | |
| Coronavirus | |
| Rabies | |
| Cat Viruses | |
| *Feline rhinotracheitis* virus | |
| *Feline calicivirus* | |
| Panieukopenia virus | |
| Feline leukemia virus | |
| Feline infectious peritonitis virus | |
| Rabies | |
| Swine viruses | Swine Bacteria |
| Transmissible gastroenteritis | Pasturella |
| Rotavirus | Erysipelas |
| Parvovirus | Leptospira sp. |
| Pseudorabies | Hasmophilus sp. |
| | Bordetella |
| | Tetanus toxoid |

TABLE 4-continued Veterinary vaccines Horse Viruses

*Equine encephalomyelitis*
Equine influenza
*Equine rhinopneumonitis*
Tetanus toxoid
Rabies "Live" virus particles may also be used as core material, in the microcapsules of this invention, for later release in vivo, to stimulate the immune system of animals. There are, in fact, vaccines made from live viruses. Examples of these are vaccinia viruses, and rotaviruses, among others. These two types of virus represent the two major categories of virus, enveloped and non-enveloped viruses. Non-enveloped viruses, such as rotavirus, poliovirus, and adenovirus, among others, are less susceptible to drying agents, detergents and surface cleansing agents than are enveloped viruses. As a result non-enveloped, but not enveloped, viruses survive well when present in sewage and on environmentally contaminated surfaces. Enveloped viruses, which due to their surface lipid bilayer are not as sturdy as non-enveloped viruses, are susceptible to break-down by contact with agents, such as those described above. DNA segments are relatively easily inserted into vaccinia virus. The rotavirus, on the other hand, is known to cause severe and sometimes fatal diarrhea in humans, particularly in infants. This technology is extended herein to viruses other than the two described above, and other microorganisms which cause disease in humans and/or other animals.

Typically, the microcapsules of the invention have varied sizes. One preferred group has a diameter of about 0.1 to 2,000 microns. Among these, preferred are those having a median volume diameter of about 100 to 1,000 microns, others having a median volume diameter of about 10 to 100 microns, and still others having a median volume diameter of about 1 to 100 microns. However, other sizes are also contemplated within this invention. When a large number of microcapsules are collected in a composition, they may have a variable particle size. Particularly preferred is the range of about 0.1 to 10 microns which encompasses the size range of respirable particles, which will travel to the alveoli, as well as the particle size that is taken up by gut-associated lymphatic tissue. In some instances, however, better results are obtained when the particle size distribution is more uniform, e.g., within less than about a 20% standard deviation of the median volume diameter, and still more uniform or within about 10% of the median volume diameter, determined as described is Example 1 below.

The microcapsules of the invention may be provided in suspension, e.g., in an aqueous medium, or in dry form, optionally in lyophilized form, in reconstituted form, in sterile form, and in containers of different volumes. Depending in part on the degree to which manufacturing fluid is removed and in part on the nature of the core solute, the aqueous core microcapsules may be collected as a free-flowing suspension, a viscous flowable concentrate, a paste, a friable flake or, with further treatment, as a lyocake. Lyophilization is particularly desired to provide stable microcapsules with highly water soluble core materials. Once encapsulated, core materials are protected from the environment. Water-soluble core materials, however, may be slowly released from the microcapsules by suspending the capsules in an aqueous medium, into which the core material can actively diffuse through the semi-permeable microcapsule walls. In general, for any particular wall-forming reactants, highly water-soluble core materials are released more rapidly than are poorly water-soluble core materials. In addition, in general, substances of low molecular weight are released more rapidly than substances of higher molecular weights. Conversion of the microcapsules to lyocakes and resuspension in aqueous media is preferred.

The microcapsules of the invention may also have an enteric coating added on top of the capsular wall for protection against harsh environmental conditions, e.g., proteolytic enzymes and high acidity, as is found in mammalian gastric juice. Examples of enteric coating materials are cellulose acetate phthalate, hydroxypropyl methylcellulose phthalate, polyoxyethylene cross-linked polyacrylic acid, polyoxyethylene cross-linked polymethacrylic acid, polyvinyl acetate and glyceryl monostearate, and poorly water-soluble homologs having a water solubility of less that 50 mg/1 at 37° C., among others. The materials and methods for adding enteric coatings to formulations are known in the art and need not be fully described herein. (Remington's Pharmaceutical Sciences, 17th Ed., Alphonso R. Gennaro, Ed., Mack Publishing Company, Easton, Pa. (1985)). The rapid release of encapsulated materials may be accomplished by adding to an aqueous suspension of the microcapsules a water soluble salt, either as solid or as a solution. In either case, the salt employed must be capable of reacting with the insoluble film to yield water-soluble ionic products in a manner analogous to the reverse of the film forming reaction. The film forming reaction is a reversible reaction, and slow release of soluble small molecules is attained through their gradual diffusion through the microcapsular walls. The diffusion rate will depend on the size and solubility of the diffusing species, and on the thickness and density of the capsular wall. Thus, in addition to providing rapid release of a core ingredient, the present technology may also be applied to provide a controlled slow-release of soluble encapsulated materials. Sustained and/or controlled release formulations of the invention may be prepared of a variety of drugs for topical application, e. g., skin and mucosa, or for systemic dosing, e. g., oral and parenteral routes, including those usually employed for the administration of drugs, vaccines and tolerogens, including intraocular, intranasal, buccal, oral, inhalation, rectal, subcutaneous, intramuscular, intra-arterial, intravenous, and intraperitoneal. This invention may also be used to prepare live virus vaccines for parenteral delivery. Both purified virus and viral tissue culture suspensions may be utilized especially well, when the separation of viral particles is not desired.

The preparation of the capsules and microcapsules of the invention is generally conducted by first preparing suitable capsules and microcapsules carrying as core material(s) an appropriate active agent(s), such as an anti-cancer or antibiotic agent, a radionuclide, an enzyme inhibitor, a magnetic material, and the like, which were more thoroughly described above. Thereafter, the peptide(s) are attached to the capsular wall, either directly, through a small molecule or bridge, or by means of a linking member of a binding pair, such as avidin, streptavidin, antibodies, antigens, immunoglobulin G, or analogous linking agents. These agents are members of a linking pair, and one of the members, e.g., avidin, may be attached to the capsular wall surface, while preserving free its binding site for binding of the other member. Finally, an appropriate lectin, antibody or other peptide, having specificity for its binding pair counterpart and/or a target macromolecule, cell, or tissue, is attached to the other member of the binding pair, e. g., biotin, antigen, antibody, p-hydroxy benzeneazobenzoic acid, protein A, or protein G. For example, a lectin may be attached to biotin. A number of lectins and antibodies specific to epitopes or cell surface markers are commercially available, either in native or biotinylated form. If a desired biotinyl derivative of a peptide is not commercially available, it may be attached to a biotin residue, or other similar peptides using commercially available biotinylating or peptide-attaching agents. If the peptide, e.g., a monoclonal antibody of a pre-determined specificity, were not available, it may be prepared and then biotinylated following known procedures. (Rivnay et al., "Use of Avidin-Biotin Technology for Liposome Targeting", in Methods in Enzymology, 149, pp. 119–123, Academic Press Inc. (1987); Yamada et al., Biochemistry 20: 4836–4842 (1981); Staros et al., Analytical Biochem. 157: 220–222 (1986); Green, N. M., "Avidin", Adv. Protein Chem., pp. 85–133 (1975)).

The linking member-peptide complex, e.g., biotin-lectin, protein A-lectin, protein G-antibody, biotin-antibody, and the like, is then allowed to complex with the microcapsules already derivatized with the other member of the pair is, e.g., avidin. This spontaneous reaction is mostly completed in a few hours upon incubation in aqueous medium at room temperature. The surface modified microcapsules are thus ready for use. The technology leading to the manufacture of the targeted microcapsules is easy and reproducible, the reactions are mild, may be conducted in aqueous medium at room temperature, and are completed in a short period of time, e.g., less than 16 hours. The avidin-carrying microcapsules were shown to bind strongly the biotinyl derivatives of several peptides, e.g., lectins, monoclonal antibodies, and labeling reagents, e.g., fluorescein, in an aqueous medium. The thus modified capsules have been shown to bind specifically to the respective carbohydrates with substantially complete exclusion of other carbohydrates. The reactions for attaching one member of the binding pair, e.g., avidin, to the capsular wall, and for attaching the other member of the binding pair to the targeting peptide(s), e.g., biotin-peptide derivatives, are extremely gentle and unlikely to alter, modify, or denature active macromolecules, such as enzymes, antibodies, vaccines, and the like. The primary peptide-derivatized, avidin-derivatized, microcapsules represent a unique common intermediate for the preparation of a wide range of particles having specific binding properties. Similarly, other linking agents, e.g., protein A or G, utilized in the context of the invention have the same ability. Contrary to the requirements of other types of technologies, the present capsules and microcapsules may be retargeted without de novo manufacturing for each different cell or tissue-specific targeting peptide. In fact, the overall preparation of the capsules and microcapsules, and the primary peptide-derivatization with a linking agent, e.g., avidin, protein A or G, are common to all targeting derivatives.

A composition of matter which comprises a plurality of capsules or microcapsules in accordance with this invention is also provided herein. The microcapsules present in the composition generally have a particle size distribution of up to about 20% standard deviation from the median volume diameter, and preferably about 15% or less. The composition may further comprise a carrier, such as biologically-acceptable carriers, pharmaceutically-acceptable carriers, and others that are essentially harmless to the capsule material, to the peptides, and to the core materials. The core loading capacity of the capsules and microcapsules of this invention is significantly higher than that of other microcapsular forms known in the art, including liposomes, polyanhydride capsules, and polylactide-coglycolide microspheres. Also higher is their efficiency of capture of the active material(s) during manufacture. This is attained without costly or highly specialized equipment, and by an easily implemented process, utilizing mild conditions, which spare the targeting peptides, the capsular wall, and the core macromolecules. The present invention is a clear improvement on prior art technology encompassing non-targeted microcapsules of all kinds, and even over targeted systems, such as targeted liposomes, and the like, described above. The present capsules and microcapsules are prepared under mild conditions at or below room temperatures whereas other particulate delivery systems such as liposomes, novasomes, polylactide-coglycolide spheres, polyanhydride particles, cochleates, and the like, which require one or more steps that are generally deleterious to the activity(ies) of core ingredients, such as the use of organic solvents. Organic solvents may alter the efficacy of core ingredient(s), such as proteins, by, for example, reordering their tertiary structure. Some systems require vigorous mechanical mixing, which may damage fragile molecules, particularly proteins, to disperse or suspend active agents contained in a solvent which is immiscible with another solvent. Other systems generate new interfaces between immiscible liquids and denature proteins. When the solvents used are volatile, they generally need to be removed with heat, which is detrimental to many fragile molecules, such as peptides.

The targeted microcapsules of the invention may be prepared by suspending or dissolving aqueous core microcapsules, whose walls comprise the reaction product of a polymer comprising a plurality of anionic residues, or a salt thereof and a monomer with a plurality of amine residues, a salt thereof, mixtures thereof, or mixtures with monoamines, the walls having an excess of either anionic or amine residues, in an aqueous medium. Thereafter, the peptide(s) is (are) contacted with the microcapsules in the aqueous medium under conditions effective to attach the peptide(s) to the excess residues on the microcapsule walls and obtain peptide-carrying microcapsules. When the primary peptide(s) added is a member of a binding pair, the targeting peptide is separately reacted under appropriate conditions to the other member of the linking pair. The peptide may be linked to the capsular wall by means of a small molecule linking agent, such as sulfosuccinimidyl-4-N(maleimidomethyl)-cyclohexane-1-carboxylate, and the like, under generally known conditions. (Hashida, S., et al., J. Applied Biochem. 6: 56–63 (1987)). Briefly, one reactive site of a heterobifunctional linking agent is allowed to react with the excess amino or carboxylate groups of the microcapsule under conditions which do not promote the reaction of the second reactive site of the linking agent. Then, the peptide or protein is added to the microcapsule suspension, and the reaction conditions are adjusted to activate the second reactive site of the linking agent to allow it to combine with the protein or peptide. More specifically, using sulfosuccinimidyl-4-N (maleimidomethyl)-cyclohexane-1-carboxylate as the example of bifunctional linking agent, the following may be conducted. The linking agent is dissolved in an aqueous phosphate buffer solution, pH 7.0–7.5, a pH range in which the sulfosuccinimidyl ester linkage is readily subject to nucleophilic attack. One or more capsules or microcapsules, prepared with an excess of amino groups on its (their) surface, then is added to the solution of linking agent and allowed to incubate for about an hour or more. Free amino groups present on the surface of the capsular surface exert a nucleophilic attack on the ester bond of the linking agent, splitting N-hydroxy sulfosuccinimide off and generating a new amide bond between the capsular amino group and the linking agents. The peptide or protein to be attached to the capsular surface then is added to the capsule suspension and the pH value of the reaction mixture adjusted to a pH about 6.5. At this pH, the maleimide group is activated and reacts quickly and specifically with any free sulfhydryl groups of the peptide or protein, thereby connecting the chain of bonds from the capsular surface through the new amide bond to the linking agent and then through the thioether bond to the peptide or protein. Alternatively, and preferably, an amide linkage may be generated to connect the peptide or protein directly to the capsular surface. In such an approach, the peptide or protein to be attached to the capsular surface is dissolved in an aqueous suspension of the capsules(s) or microcapsule(s) displaying an excess of amino groups on the surface. A solution of a carboxyl group activating agents, e.g., N-hydroxysulfosuccinimide, 1-ethyl-3-3-dimethyl amino propyl carbodimide, is added to the solution/suspension and the mixture is incubated at or below room temperature. During incubation, the carbodiimide reagent promotes the formation of an O-acylurea from the carboxylate groups of the peptide or protein. The O-acylurea, an activated ester, undergoes a nucleophilic attack by the hydroxysuccinimide reagent to form an iminoester which then reacts with amino groups of the capsular surface, forming a new amide bond between the capsular amino group and the carboxylic acid group of a peptide/protein while regenerating the hydroxysuccinimide reagent.

If a linking protein pair, such as avidin-biotin is utilized, the biotinylated derivative of the targeting peptide may be obtained commercially or prepared by methods known in the art. (Hoffman, K., et al., J. Am. Chem. Soc. 100: 3585–90 (1978); Lee, W. T., and Conrad, D. H., J. Exp. Med. 159: 1790–95 (1984)). Briefly, most reagents used to fix a biotinyl residue onto a protein or peptide employ N-hydroxysuccinimide or a water-soluble derivative thereof esterified to the carboxylic acid group of biotin. The resulting amino ester reagents react with free amino groups of peptides and proteins in the manner described above.

The second member of a binding pair-peptide(s), or derivatized targeting peptide(s), of a pre-determined specificity may then be contacted with the primary peptide-carrying microcapsules in an aqueous medium under conditions effective to attach or complex them. The targeting peptide(s) may be lectins, antibodies, such as immunoglobulins and monoclonal antibodies, and antigens of defined specificity, and the like, may be bound directly by the primary peptide(s), or be attached to the second member of the binding pair, e.g., biotin, protein A, protein G, antigens and antibodies.

The reaction of the peptide with the excess moieties on the capsular wall surface is preferably conducted by adding an aqueous suspension or solution of the peptide(s), e. g., avidin, streptavidin, lectin, antibody, and other proteins or fragments thereof, to a suspension of the microcapsules at a temperature of about 4° to 40° C, more preferably at about 10° to 25° C., more preferably in the presence of a small molecule linker, such as N-hydroxysulfosuccinamide or ethlydimethylaminopropyl carbodiimide, and more preferably in an about equimolar proportion and with gentle mixing. This is conducted under conditions which provide gentle mixing of the peptide/protein and expose all capsular surfaces to the reaction medium while avoiding strong agitation or exposure of the peptide/protein to freshly formed air/water interfacial boundaries. These conditions are conveniently met by slowly rotating a well-filled vessel containing the reaction mixture with a clinical rotator at a nominal speed of, e.g., about 4 r.p.m. The reaction of the derivatized targeting peptide with primary peptide(s)-carrying capsules may be conducted by adding an aqueous suspension or solution of the derivatized peptide(s) to an aqueous suspension or solution of the primary peptide(s)-carrying microcapsules at a temperature of about 4° to 40° C., and more preferably about 10° to 25° C., using conditions similar to those described above, which ensure gentle mixing of the reactants and expose the capsular surfaces to the reaction medium.

Although different methods of preparing the microcapsules themselves may be utilized, preferred is the method disclosed in U.S. patent application Ser. No. 08/228,481, the pertinent portions of which are incorporated herein by reference. Briefly, the dissolved microcapsules may be formed by selecting an anionic polymer or salt thereof and a monomer provided with a plurality of amine residues, a salt thereof, mixtures thereof, or mixtures thereof with monoamines, and allowing the formation of stable microcapsules when, e.g., droplets of, the anionic polymer is (are) added to an aqueous solution of the amine. More specifically, the microcapsules may be formed by dissolving the anionic polymer or salt thereof in an aqueous medium, preferably to a viscosity of about 2.5 to 50 centipoise or greater; dissolving the amine or salt thereof in a second aqueous medium; optionally forming a droplet of the anionic polymer solution; and adding the polymer droplet to the amine and allowing the reaction to occur and to form microcapsules in the form of an enclosing film comprising a salt of the polymer(s) and the amine(s). A large number of capsules may be formed by repeatedly performing these steps, while avoiding contact between successive droplets until each droplet is completely formed. The microcapsules may then be preserved in suspension, e.g., in an aqueous medium, or harvested and dried and/or lyophilized for storage.

The formation of the drops may be performed while applying pulsating energy provided by an acoustic signal to a downwardly flowing stream of the anionic polymer solution. To obtain microcapsules of substantially uniform diameter, this step may be conducted by supplying the polymer solution in the form of a fine spray. In one preferred embodiment, the polymer droplets are formed of a substantially uniform dimension by mechanically disrupting a thin flowing stream of the polymer solution prior to its addition to the amine. The thin flowing stream of the anionic polymer solution may be disrupted by sonic stimulation. When core-loaded microcapsules are desired, an aqueous solution or suspension of an active agent, e.g., a drug, vaccine or pesticide and, if desired, an adjuvant, photoprotectant or colorant, among others, may be dissolved or suspended in an aqueous solution of, e.g., the sodium salt of a suitable anionic polymer. The resulting solution/suspension is then dispersed, as droplets, in an aqueous solution of a suitable amine, or salt or mixtures thereof. At the apparent interface of the polymer droplets and amine solution, a salt-exchange reaction takes place. This reaction forms poorly soluble salts of the amine and the polymer and more or less spherical beads or capsules containing the active component precipitate. The anionic polymer and reactant amine may be chosen from those which, on reaction with one another, will rapidly form a poorly soluble precipitate. In this manner, the droplets are formed before the polymer diffuses sufficiently to appreciably distort the droplet shape, or the concentration of the anionic polymer falls below that required to form a film.

Thus, although employing polymer solutions of high viscosity is not necessary, the polymer should be capable of rapid diffusion to, and reaction at, the pseudophase boundary defined by the polymer droplet. A convenient means of dispersing the anionic polymer droplets containing an active ingredient, in the amine solution, is to allow an aerosol of the polymer solution to fall onto/into the amine solution as the latter is stirred. A Bernouli-type nebulizer, when used to generate the aerosol, will result in microcapsules with a relatively wide (Gaussian distribution of particle sizes about the mean, with variation coefficients of about 25 to 50 %. If narrower size distributions are desired, an acoustically pulsed droplet generator, such as the one described in U.S. patent application Ser. No. 08/228,481, may be used to provide highly uniform microcapsules, with diameter variability coefficients of about 5%. The microcapsules prepared by the method described above, particularly those of extremely narrow size distribution, at selectable median sizes, may be prepared with the aid of an apparatus, such as the one described in U.S. application Ser. No. 08/228,481, the pertinent portions of which are incorporated herein by reference. This is of importance, for example, in microcapsules intended for injection, for uptake by lymphatic tissues (a subset of which are Peyer's patches), or the bronchus-associated lymphatic tissue of the respiratory system. When the microcapsules are intended for intravenous injection, their size is small enough to pass through capillary beds, e.g., less than about 5 microns in diameter, when intended for inhalation, also less than about 5 microns, and to reach deep alveolar sites, preferably less than about 2 microns. The Peyer's patches require particles of less than about 10, and preferably about 5 microns in diameter. Microcapsules of varied sizes may be produced herein, with standard deviations from the mean of less than about 0.5 micron, around the mean volume diameter of about 5 microns.

This invention is exemplified herein by a number of experimental demonstrations, which are described below.

EXAMPLE 1

Spermine Alginate Capsule and Microcapsule Preparation

The spermine alginate capsules were prepared by dropwise addition of nominally 40 ul droplets of a 1% (w/v) aqueous sodium alginate solution to a 1% (w/v) aqueous spermine hydrochloride solution at room temperature. Addition of sodium alginate to spermine hydrochloride was accomplished using a peristaltic pump operating at a rate of approximately 1 ml/min. The sodium alginate droplets were allowed to fall a distance of approximately one inch. The spermine hydrochloride solution was gently stirred using a magnetic stir bar and plate during addition of sodium alginate. The capsule forming procedure was halted after approximately two volumes of the sodium alginate solution had been added to one volume of the spermine hydrochloride solution.

The resulting suspension of nominally 2.9 mm diameter capsules was gently stirred for 24 hours at room temperature to allow equilibration. The capsules were then allowed to settle, the supernatant was removed and the capsules were washed three times with distilled water to remove unreacted reagents. The capsules were stored in water at 4° C. until used.

Spermine alginate microcapsules were prepared by addition of nominally $8\times10^{-7}$ ul droplets of a 0.05% (w/v) aqueous sodium alginate solution to a 0.05% (w/v) aqueous spermine hydrochloride solution at room temperature. Sodium alginate droplet formation was accomplished by pumping the sodium alginate solution at a rate of approximately 1 ml/min through a glass capillary which was firmly pressed against an ultrasonic probe operating at 20 KHz and 50 Watts. The microcapsule forming procedure was halted after approximately two volumes of the sodium alginate solution had been added to one volume of the spermine hydrochloride solution. The resulting suspension of microcapsules was gently stirred for 24 hours at room temperature to allow equilibration. The microcapsules were then allowed to settle, and the supernatant removed, and the microcapsules were washed three times with distilled water to remove unreacted reagents. The microcapsules were stored in water at refrigerator temperature until used.

Size Analysis of Spermine Alginate Capsules and Microcapsules

The spermine alginate capsules were sized using a micrometer, and deformed or irregularly shaped capsules were discarded. Linear measurements of 10 capsules were made along two of the three capsular axis. The average capsular diameter, standard deviation and surface were then calculated from these data.

The average size and size distributions of freshly prepared batches of spermine alginate microcapsules were determined using a Coulter counter (Coulter Corp., Hyaleah, Fla.) equipped with a 30 um aperture tube. The reagent solutions were passed through a 0.22 um filter prior to microcapsule formation to decrease background counts. Spermine hydrochloride 0.05% (w/v) was used as the Coulter counter electrolyte to establish and maintain a constant ionic strength across the counter electrode during operation. Triplicate counts were made at settings corresponding to equivalent spherical diameters of 1, 2, 3, 4, 5, 6, and 7 um. Histograms of size distributions of the batches of spermine alginate microcapsules were obtained by displaying the median microcapsule diameters of the size intervals measured in microns on the abscissa, and the frequencies measured in microcapsule counts on the ordinate (Figure not shown). In all tests, the distributions were not centered about the mode, which would indicate a normal distribution, but were skewed to the right, which suggests a log-normal distribution (Edmonson, I. C., Particle Size Anaylsis, in Advances in Pharmaceutical Sciences, London & N.Y., Academic Press, p. 112 (1967)). To confirm the log-normal nature of size distributions of the batches of microcapsules, the microcapsule diameters were plotted on the abscissa and the % oversize frequencies of the microcapsules on the ordinate of a log-probit graph (Martin, A., Micrometrics, in Physical Pharmacy, 4th Ed., Philadelphia & London, Lea & Febiger, p. 4728 (1993)(Figures not shown)). The geometric mean of the microcapsular diameters was taken to be the point where the line of best fit crosses the 50% oversize line of the ordinate. The geometric mean diameter of the batches of microcapsules was determined to be 3.6, 4, and 3.8 microns, respectively. The geometric standard deviation of the microcapsular diameters was calculated from the quotient of the ratio 16% oversize/50% oversize.

Attachment of Avidin to Spermine Alginate Capsule Surfaces

Avidin was conjugated to the surface of spermine alginate capsules. Separate groups of 5 spermine alginate capsules were transferred to screw cap test tubes containing 5 ml equimolar concentrations of ethyl—(3- dimethylaminocarbodiimide (EDC), N-hydroxysulfosuccinimide (NHSS), and avidin. The capsules and the reactants were mixed on a clinical rotator at a rate of 4 rpm, and allowed to react for 16 hours. The reaction of a group of capsules was then halted by removing the reagent solution and washing the capsules 3 times with 0.5 ml distilled water each time. The avidin-coated capsules were stored in water at refrigerator temperature until used.

The influence of the concentration of the reagents on the extent of avidin binding was determined by varying the equimolar concentrations of avidin, EDC, and NHSS, from 0 to 6 uM and mixing for 16 hrs. The capsules were subsequently assayed for bound avidin as described below.

The quantity of avidin bound to the surface of the spermine alginate capsules, as a function of the quantity of avidin, EDC, and NHSS used in the reaction, was measured. The results of this study are shown in Table 5 below.

TABLE 5

Influence of Avidin, EDC, and NHSS Concentration on Conjugation of Avidin to Spermine Alginate Capsule Surfaces (n = 5)

| Initial Conc. Avidin, EDC, and NHSS | Surface Bound Avidin | | Standard Deviation | |
|---|---|---|---|---|
| nM | mg/cm$^2$ | nmole/cm$^2$ | mg/cm$^2$ | nmole/cm$^2$ |
| 0 | 0.022 | 0.33 | 0.015 | 0.23 |
| 1.5 | 0.168 | 2.5 | 0.012 | 0.18 |
| 2.25 | 0.328 | 4.95 | 0.067 | 1.0 |
| 3.0 | 0.402 | 6.0 | 0.033 | 0.49 |
| 3.75 | 0.362 | 5.4 | 0.025 | 0.36 |
| 5.25 | 0.382 | 5.7 | 0.058 | 0.86 |
| 6.0 | 0.362 | 5.4 | 0.033 | 0.5 |

The time course of the avidin conjugation reaction was determined by allowing separate groups of capsules to react with that concentration of avidin, EDC, and NHSS giving maximum avidin binding in the previous experiment for timed intervals of 0.5, 1, 2, 4, 8, 16, 24, and 46 hours. The capsules were subsequently assayed for bound avidin as described below. For further experiments, capsules were prepared by allowing the avidin conjugation reaction to proceed for the timed interval which provided sufficient yield of avidin-coated capsules.

Avidin Assay

Avidin was assayed according to the method described by Green (Green, N. M., Biochem. J. 94: 23c–24c (1965)). Avidin lacks an analytically exploitable chromophore, but induces a bathochromic shift in the absorption spectrum of the dye, 2-(4'hydroxyazobenzene) benzoic acid (HABA) when these two reagents are mixed in solution.

Avidin was assayed by adding a stoichiometric excess of HABA to the analyte solution and measuring the absorbance of the solution at the wavelength characteristic of the avidin-HABA complex (about 500 nm). The absorbances were then converted into avidin quantities with the aid of a linear regression equation generated from a daily prepared, 5-point standard curve. 5 capsules were first used individually in 2 ml of 0.6% (w/v) phosphate buffered saline (PBS)(pH 6.0), and 1 ml 0.4 mM HABA dissolved in a separate quantity of the same phosphate buffer was then added to the analyte solution. The volumes of the analyte solutions were adjusted to 5 ml with the same buffer and the absorbances were measured at 500 nm.

The quantity of avidin coupled to the surface of the spermine alginate capsules as a function of time was also measured. The results of this study can be seen in Table 6 below.

TABLE 6

Avidin Coupled to Surface of Spermine Alginate Capsules as Function of Time (n = 5)

| Time (hrs.) | Bound Avidin | | Standard Deviation | |
|---|---|---|---|---|
| | mg/cm$^2$ | nmole/cm$^2$ | mg/cm$^2$ | nmole/cm$^2$ |
| 0.5 | 0.077 | 1.16 | 0.019 | 0.29 |
| 1.0 | 0.142 | 2.13 | 0.063 | 0.95 |
| 2.0 | 0.142 | 2.13 | 0.03 | 0.45 |
| 4.0 | 0.256 | 3.84 | 0.38 | 0.49 |
| 8.0 | 0.278 | 4.17 | 0.026 | 0.39 |
| 16.0 | 0.33 | 4.95 | 0.068 | 1.0 |
| 24.0 | 0.369 | 5.54 | 0.048 | 0.72 |
| 46.0 | 0.438 | 6.75 | 0.045 | 0.68 |

Binding of Biotinylated Lectins to Avidin Coated Spermine Alginate Capsules

To bind the lectins to the surface of the capsules, the avidin-coated capsules were incubated for 2 to 16 hours in 1 ml aqueous solutions containing the maximum quantity of biotinylated lectin which may be expected to be bound to the surface of the avidin-coated capsules, as determined below. The binding of biotinylated lectins to avidin-coated capsules was assayed turbidimetrically. The biotin-lectin conjugates lack an analytically exploitable chromophore but form a precipitate when added to aqueous solutions of avidin. The extent of precipitation of the biotin-lectin-avidin complex was monitored using a spectrophotometer to measure apparent absorbance, i.e., turbidance, in a manner analogous to classical agglutination assays. To achieve adequate sensitivity, the turbidance measurements were made at the shortest wavelength of visible light attainable with the instrument, or 360 nm.

To establish a basis for the biotin-lectin binding assay, equimolar aqueous solutions of biotin, biotin-concanavalin A, and concanavalin A were added separately, in 20 ul increments to 2 ml aqueous solutions of avidin, lysed spermine alginate capsules, and lysed avidin-coated spermine alginate capsules. The resultant nine different mixtures were examined spectrophotometrically after each addition for the presence of a precipitate.

The apparent stoichiometry of binding of the biotinylated lectins, listed in Table 7 below, to the avidin-coated capsules was determined by lysing 5 avidin-coated capsules in PBS separately, and titrating them to the turbidance end point at 360 nm with freshly prepared solutions of the biotinylated lectins.

The addition of aqueous concanavalin A to aqueous avidin in control experiments and/or to an avidin-coated spermine alginate capsule lysed in PBS, yielded a cloudy precipitate. The precipitate was an avidin-concanavalin A complex in which concanavalin A was bound to the carbohydrate portion of avidin. Other lectins, which possess affinities for saccharides also found in avidin, also formed precipitates when added to avidin-containing solutions. The binding of a lectin to the carbohydrate portion of avidin may limit its carbohydrate binding capacity and, consequently, the bioadhesive ability of the lectin-coated microcapsules. In addition, the binding of a lectin to the carbohydrate portion of avidin may lower the apparent stoichiometry of the biotin-lectin-avidin complex based on the avidin-biotin interaction. Streptavidin, unlike avidin, contains no carbohydrate and, thus, in all likelihood, leaves a greater fraction of some lectins available to react with target epitopes. The biotinylated lectins utilized in the experimental disclosure included herein, were selected based on their availability, molecular weight, carbohydrate specificity, and cost. The addition of the biotinylated lectins to the lysed avidin-coated capsules was made in 20 ul increments at approximately 1 min. intervals. The titrand solutions were stirred with a wire loop following the addition of each titrant aliquot. The quantity of the biotinylated lectin corresponding to the point where a plot of the titration curve abruptly decreases in slope was interpreted as the titration end point representing the maximum quantity of biotinylated lectin which may be bound to the surface of the avidin-coated capsules. Examples of biotinylated lectins utilized experimentally are shown in Table 7 below together with the quantity of each bound to avidin-treated capsular surfaces.

TABLE 7

Binding of Biotinylated Lectins to Avidin
- coated Spermine Alginate Capsules (n = 5)

| Biotinylated Lectin | Molecular Weight[1] | Quantity Bound[2] (nmole/cm$^2$) |
|---|---|---|
| Wheat Germ Agglutinin | 36,000 | 6.82 |
| Lentil Agglutinin | 49,000 | 4.24 |
| Succinylated Concanavalin A | 56,000 | 5.83 |
| Coral Tree Agglutinin | 57,000 | 5.64 |
| Tomato Lectin | 71,000 | 4.73 |
| Concanvalin A | 102,000 | 1.99 |
| Hairy Vetch Lectin | 110,000 | 1.80 |
| Red Kidney Bean Lectin | 115,000 | 2.90 |
| Soybean Agglutinin | 120,000 | 3.67 |
| Peanut Agglutinin | 120,000 | 2.88 |

[1]MW: From suppliers' literature
[2]Quantity bound to surface of intact avidin-coated spermine alginate capsules Example 2

Binding of Biotin-Fluorescein to Avidin Coated Spermine Alginate Capsules

Avidin coated capsules were prepared as described in Example 1 above. To bind fluorescein-biotin to the surface of the capsules, avidin-coated capsules were incubated for 2 to 4 hours in 5 ml aqueous solutions of fluorescein-biotin ranging in concentrations from 0 to 40 micromolar. The apparent stoichiometry of binding of biotin-fluorescein to avidin-coated capsules was determined by incubating separately 5 avidin-coated capsules for 16 hrs. in 5 ml of one of a series of biotin-fluorescein solutions ranging in concentration from 0 to 70 uM. The supernatant was then removed by aspiration, and the capsules washed 3 times by resuspension in fresh 1 ml distilled water each time. The capsules were then individually lysed in 2 ml PBS, and the solutions assayed spectrophotometrically at 493 nm. The absorbance measurements were converted to umoles with the aid of a regression equation generated from a five point standard curve.

Biotin-fluorescein was bound to avidin-coated spermine alginate capsules. The quantity of biotin-fluorescein bound to the capsule surfaces was found to increase linearly with increasing concentrations of biotin-fluorescein until a plateau was observed, starting at the points corresponding to 21 uM and 15 nM/cm$^2$, respectively. The plateau is believed due to a saturation of free biotin binding sites. The present results demonstrate that the avidin-biotin link may be used to attach materials other than lectins to the surface of spermine alginate capsules or microcapsules. The results are shown in Table 8 below.

TABLE 8

Binding of Biotin-fluroscein (B-F)
to Avidin-coated Spermine Alginate
Capsules (n = 5)

| Free B-F Conc. | | Bound B-F | | Standard Deviation | |
|---|---|---|---|---|---|
| ug/ml | uM | ug/cm$^2$ | nmole/cm$^2$ | ug/cm$^2$ | nmole/cm$^2$ |
| 0 | 0 | 0 | 0 | 0.05 | 0.09 |
| 3.9 | 6.95 | 1.74 | 3.09 | 0.21 | 0.37 |
| 7.72 | 13.7 | 5.23 | 9.3 | 0.50 | 0.89 |
| 11.6 | 20.5 | 8.37 | 14.9 | 0.42 | 0.74 |
| 15.5 | 27.7 | 8.37 | 14.9 | 0.94 | 1.67 |
| 19.4 | 34.6 | 10.1 | 18.0 | 0.49 | 0.87 |
| 29.4 | 52.3 | 10.9 | 19.4 | 0.45 | 0.80 |
| 39.4 | 70.1 | 10.9 | 19.4 | 0.57 | 1.01 |

B-F: Biotin-fluorescein

EXAMPLE 3

Binding of $^{14}$C-labeled Carbohydrates to Lectin-Coated Spermine Alginate Capsules The apparent binding stoichiometry of mannose to lectin-coated capsules was determined by coating separate batches of capsules with surface saturating quantities of concanavalin A, peanut agglutinin, and wheat germ agglutinin respectively. Three lectin-coated capsules were then incubated for 16 hrs. in 1 ml of one of a graded series of aqueous $^{14}$C-labeled mannose (57.0 mCi/mmole) solutions ranging in concentrations of 0 to 0.0175 mM. The mannose solution was then removed by aspiration, and the capsules washed three times by resuspension in fresh 1 ml distilled water each time. The capsules were then removed and placed into separate scintillation vials containing 4 ml scintillation medium. The beta particles emitted were counted using a liquid scintillation counter, and converted to molar quantities with the aid of the regression equation generated from a 6-point standard curve.

The apparent binding stoichiometry of galactose to the lectin-coated capsules was determined by conducting the above experiment with capsules coated with the same 3 lectins using in place of $^{14}$C-labeled mannose, $^{14}$C-labeled galactose (48.3 mCi/mmole) in concentrations ranging from 0 to 0.02 mM, and the counts were converted to molar quantities with the aid of the regression equation generated from a 6-point standard curve.

EXAMPLE 4

Binding of $^{14}$C-labeled Carbohydrates to Lectin-coated Spermine Alginate Capsules Two different $^{14}$C-labeled carbohydrates, mannose and galactose, bound to the spermine alginate capsules carrying one of three different biotinylated lectins: concanavalin A, peanut agglutinin, and wheat germ agglutinin. (Results not shown).

The relative mannose-binding capacities of the three capsule-bound biotinylated lectins was found to be as follows.

Concanavalin A>Peanut Agglutinin>Wheat Germ Agglutinin

These findings show that capsules coated with a surface-saturating amount of concanavalin A adhere more strongly to tissues expressing mannose on their surface than capsules coated with surface saturating quantities of peanut agglutinin or wheat germ agglutinin. Similar experiments were conducted with galactose and the lectins concanavalin A, peanut agglutinin, and wheat germ agglutinin. (Results not shown). The rank order of the galactose binding capacity of the two capsular bound biotinylated lectins was found to be as follows.

Concanavalin A>Wheat Germ Agglutinin>Peanut Agglutinin

These findings show that capsules coated with a surface saturating quantity of concanavalin A would adhere more strongly to tissues expressing galactose on their surface than capsules coated with surface saturating quantities of wheat germ agglutinin or peanut agglutinin. A comparison of the data obtained indicates that concanavalin A is only moderately more selective for mannose than galactose whereas peanut agglutinin is substantially more selective for galactose than mannose when bpound to capsular surfaces.

Completely formed capsules are white spheres approximately 2.9 mm in diameter. Separately prepared batches of spermine alginate microcapsules were sized using a Coulter counter. The average diameter of the microcapsules was found to be 3.8 microns.

Alkyl amines used to form microcapsules by interfacial precipitation with sodium alginate must possess multiple amino functionalities in order to be surface modified using the described procedures. The presence of multiple amino functionalities, as in the case of spermine, allows the EDC-NHSS mediated formation of amide bonds involving the avidin carboxylates and the spermine amines.

While this invention has been described with reference to specific, and particularly preferred embodiments thereof, it is not limited thereto, and the appended claims are intended to be construed to encompass not only the specific forms and variants of the invention shown, but to such other forms and variants as may be devised by those skilled in the art without departing from the true spirit and scope of the invention.

We claim:

1. A composition, comprising at least one microcapsule(s) comprising an aqueous core surrounded by a capsular wall having a surface provided with peptide(s) linked thereto, the peptide(s) having a free segment(s) of pre-determined binding specificity(ies) capable of selective attachment to macromolecules, cells, and/or tissues displaying on their surfaces characteristic epitopic markers and the wall comprising the reaction product of a polymer having a plurality of anionic residues and a monomer having a plurality of amine residues wherein the capsular wall comprises an excess of either said anionic or amine residues, to which the peptide(s) is (are) linked.

2. The composition of claim 1, wherein the capsular wall comprises an excess of amine residues, to which the peptide (s) is (are) linked, and said monomer includes three or more amine residues.

3. The composition of claim 2, wherein the microcapsule (s) further comprise(s) a bifunctional agent linking the excess amine or anionic residues and the peptide(s).

4. The composition of claim 3, wherein the linking agent comprises a binding pair selected from the group consisting of avidin and biotin, streptavidin and biotin, avidin and p-hydroxy-benzene-azo-benzoic acid, streptavidin and p-hydroxy-benzeneazo-benzoic acid, protein G and immunoglobulin A, G, and M, protein A and immunoglobulin A, G, and M, and antibody or antibody fragments thereof and complementary antigens, wherein the biotin and the p-hydroxy-benzene-azo-benzoic acid are linked to the segment(s) of pre-determined binding specificity(ies).

5. The composition of claim 4, wherein the linking agent comprises biotin-avidin.

6. The composition of claim 1, wherein the polymer comprises an anionic residue selected from the group consisting of reactive carboxylate, phosphate, phosphamido, sulfonate, and sulfate groups.

7. The composition of claim 6, wherein the polyanionic monomer or polymer is selected from the group consisting of alginic acid, arabic acid, cellulose sulfate, carboxymethylcellulose, carrageenans, chondroitin sulfate, heparin, polyacrylic acid, polyoxyethylene cross-linked polyacrylic acid, polyphosphazine, lactic esters of polyphosphazine, hyaluronic acid, and polyvinylcarboxylic acid.

8. The composition of claim 1, wherein the polyamine comprises di-, tri-, tetra-amines, mixtures thereof, or mixtures thereof with monoamines.

9. The composition of claim 8, wherein the polyamine is selected from the group consisting of ($C_1$–$C_{16}$) alkylene diamines, ($C_1$–$C_{16}$) alkylene triamines, ($C_1$–$C_{16}$) alkylene tetraamines, mixtures thereof, and mixtures thereof with ($C_1$–$C_{16}$) monoamines.

10. The composition of claim 9, wherein
   the polyamine is selected from the group consisting of ethylene diamine, propylene diamine, butylene diamine, pentylene diamine, piperazine, spermidine, diethylene triamine, methylene blue, and spermine; and
   the monoamine is selected from the group consisting of decylamine, dodecylamine, tetradecylamine, hexadecylamine, octadecylamine, and didecylamine.

11. The composition of claim 10, wherein the anionic polymer comprises alginic acid, and the polyamine comprises spermine.

12. The composition of claim 10, wherein the anionic polymer comprises chondroitin sulfate, and the polyamine comprises spermine.

13. The composition of claim 10, wherein the anionic polymer comprises polyacrylic acid, and the polyamine comprises diaminobutane.

14. The composition of claim 10, wherein the anionic polymer comprises arabic acid.

15. The composition of claim 1, wherein the anionic polymer has an average molecular weight greater than about 10 Kilodaltons.

16. The composition of claim 1, wherein the anionic polymer is modified by a signaling agent selected from the group consisting of fluroescein isothiocyanate, rhodamine isothiocyanate, eosin isothiocyanate, sulforhodamine acid chloride, ferritin, ferrocene carboxylic acid(s), gold conjugates, $^3$H-acetic anhydride, $^{14}$C-acetic anhydride, $^{125}$I-benzoic acid, and luciferase.

17. The composition of claim 1, wherein the peptide(s) is(are) selected from the group consisting of avidin, streptavidin, lectins, antibodies, immunoglobulin G, protein A, protein G, and antigens.

18. The composition of claim 17, wherein the peptide(s) comprises a lectin(s).

19. The composition of claim 18, wherein the lectin(s) is (are) selected from the group consisting of *Arachis hypogaea*, *Canavalia ensifonnia*, succinylated *Canavalia ensiformis*, *Lens culinaria*, *Erythina corallodendron*, *Lycopersicon esculentum*, *Vicia villosa*, *Phaseolis vulgaris*, *Gylcine max*, *Triticum vulgaris*, and *Ulex europeaus* lectins.

20. The composition of claim 17, wherein the peptide(s) comprises avidin, or streptavidin.

21. The composition of claim 17, wherein the peptide(s) comprises an antibody selected from the group consisting of IgA, IgG, IgM, and Fab and Fab' fragments thereof.

22. The composition of claim 1, wherein the microcapsule (s) further comprise(s) an active ingredient in the aqueous core.

23. The composition of claim 22, wherein the active ingredient is selected from the group consisting of polypeptide(s), non-peptide polymers, cells and fragments thereof, pharmaceutical agents, dyes, labeling agents, agricultural agents, animal health agents, magnetic materials, image-enhancing materials, pesticides, pheromones, photoprotective agents, and pigments.

24. The composition of claim 23, wherein the active ingredient comprises a polypeptide selected from the group consisting of glucose 6-phosphate dehydrogenase, calcitonin, erythropoietin, hemoglobin, interleukin, somatotropin, asparaginase, insulin, lactase, cellulose, trypsine, lipase, collagenase, streptodornase, streptokinase, tissue plasminogen activator, and *B. thuringiensis* larvacidal proteins.

25. The composition of claim 23, wherein the active ingredient comprises a non-peptidic macromolecule selected from the group comprising of heparin, analogs thereof, and anti-sense nucleotides.

26. A composition of claim 23, wherein the active ingredient comprises cells selected from the group consisting of pancreatic islet cells, hepatocytes, thyroid cells, parathyroid cells, gonadal cells, adrenocortical cells, and interleukin- and other immunomodulator-secreting cells.

27. The composition of claim 23, wherein the active ingredient comprises a pharmaceutical agent selected from the group consisting of anti-neoplastic agents, radionucleides, anti-inflammatory agents, antibiotics, anti-fungal agents, anti-helmintic agents, anti-protozoal agents, and anti-hypogylcemic agents.

28. The composition of claim 27, wherein the pharmaceutical agent(s) is selected from the group consisting of carbenacyllin, doxorubicin, naproxin, fluorouracil, prednisolone, indomethacin, tetracycline, theophylline, amphotericin B, ketoconazole, griseofulvin, diethylcarbamazine, ivermectin, praziquantel, chloroquin, pyramethamine, quinine, and nicotinamide.

29. The composition of claim 23, wherein the active ingredient comprises dyes or pigments selected from the group consisting of dextran blue, phenol red, chlorophyll, eosin, erythrosin, fluorescein, rhodamine, Texas red; and trypan blue.

30. The composition of claim 1, wherein the microcapsule (s) has (have) a diameter of about 0.1 to 2,000 microns.

31. The composition of claim 30, wherein the microcapsule(s) has (have) a diameter of about 0.1 to 10 microns.

32. The composition of claim 30, comprising a plurality of the microcapsules, the microcapsules having a particle size distribution within a standard deviation from the median volume diameter of less than about 20 %.

33. The composition of claim 1, in lyophilized form.

34. The composition or claim 1, wherein the microcapsule (s) further comprise(s) an enteric coating.

35. The composition of claim 34, wherein the enteric coating comprises a material selected from the group consisting of cellulose acetate phthalate, hydroxypropyimethylcellulose phthalate, polyoxyethylene-cross-linked polyacrylic acid, polyoxyethylene cross-linked polymethacrylic acid, polyvinyl acetate, glyceryl monostearate, and homologs thereof having a water solubility of less than about 50 mg/l at 37° C.

36. The composition of claim 1, obtained by a method comprising suspending aqueous core microcapsules, whose walls comprise a reaction product of an anionic polymer and a monomer having a plurality of amine residues, the walls also having an excess of either anionic or amine residues, in an aqueous medium, and contacting at least one peptide(s) to the microcapsules under conditions effective to attach the peptide(s) to the excess residues on the microcapsule walls and obtain peptide-carrying microcapsules.

37. The composition of claim 1, in the form of a kit further comprising instructions for its use.

38. The composition of claim 1, wherein said monomer is mixed with at least one monoamine.

39. The composition of claim 1, wherein said capsular wall is the reaction product of the salt forms of one or both of said anionic polymer and said polyamine monomer.

40. The composition of claim 2, wherein said monomer is mixed with at least one monoamine.

41. The composition of claim 36, wherein said monomer is mixed with at least one monoamine.

42. The composition of claim 36, wherein said capsular wall is the reaction product of the salt forms of one or both of said anionic polymer and said polyamine monomer.

* * * * *